(12) United States Patent
Serafino et al.

(10) Patent No.: US 10,247,832 B2
(45) Date of Patent: Apr. 2, 2019

(54) HYBRID PET / CT IMAGING DETECTOR

(71) Applicant: KONINKLIJKE PHILIPS N.V., Eindhoven (NL)

(72) Inventors: Nathan Serafino, Highland Heights, OH (US); Dane Pittock, Lyndhurst, OH (US); Jerome John Griesmer, Mentor, OH (US); Marc Anthony Chappo, Elyria, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/748,330

(22) PCT Filed: Jul. 28, 2016

(86) PCT No.: PCT/IB2016/054493
§ 371 (c)(1),
(2) Date: Jan. 29, 2018

(87) PCT Pub. No.: WO2017/025842
PCT Pub. Date: Feb. 16, 2017

(65) Prior Publication Data
US 2018/0217273 A1 Aug. 2, 2018

Related U.S. Application Data

(60) Provisional application No. 62/202,414, filed on Aug. 7, 2015.

(51) Int. Cl.
*G01T 1/16* (2006.01)
*G01T 1/161* (2006.01)
(Continued)

(52) U.S. Cl.
CPC ............ *G01T 1/1617* (2013.01); *A61B 6/032* (2013.01); *A61B 6/037* (2013.01); *A61B 6/4233* (2013.01);
(Continued)

(58) Field of Classification Search
CPC ........ G01T 1/1617; A61B 6/032; A61B 6/037
See application file for complete search history.

(56) References Cited

U.S. PATENT DOCUMENTS 6,448,559 B1 9/2002 Saoudi
2003/0108147 A1 6/2003 Kojima
(Continued)

FOREIGN PATENT DOCUMENTS

EP 1413898 4/2004
WO 2012066469 5/2012
(Continued)

*Primary Examiner* — Hugh Maupin

(57) ABSTRACT

An imaging system (102) includes a detector array (104) with a ring (106) with a first layer (110i) that detects gamma radiation and X-ray radiation and a second layer (110N) that detects only gamma radiation, wherein the first and second layers are concentric closed rings. A method includes detecting gamma radiation with a first layer of a dual layer detector in response to imaging in PET mode, detecting gamma radiation with a second layer of the dual layer detector in response to imaging in PET mode, and generating PET image data with the radiation detected with the first and second layers. The method further includes detecting X-ray radiation with the first layer in response to imaging in CT mode and generating CT image data the radiation detected with the first layer. The method further includes displaying the image data. The imaging system allows a single gantry for both PET/CT imaging.

19 Claims, 5 Drawing Sheets

(51) Int. Cl.
  *A61B 6/00*   (2006.01)
  *A61B 6/03*   (2006.01)
  *G01T 1/164*  (2006.01)
  *G01T 1/20*   (2006.01)
  *G01T 1/29*   (2006.01)

(52) U.S. Cl.
  CPC .......... *A61B 6/4241* (2013.01); *A61B 6/4266* (2013.01); *A61B 6/4275* (2013.01); *A61B 6/4291* (2013.01); *A61B 6/4417* (2013.01); *A61B 6/482* (2013.01); *A61B 6/5205* (2013.01); *A61B 6/5235* (2013.01); *A61B 6/5282* (2013.01); *G01T 1/1603* (2013.01); *G01T 1/164* (2013.01); *G01T 1/1615* (2013.01); *G01T 1/2008* (2013.01); *G01T 1/2018* (2013.01); *G01T 1/2985* (2013.01); *A61B 6/4258* (2013.01)

(56) References Cited

U.S. PATENT DOCUMENTS

| | | | |
|---|---|---|---|
| 2006/0081899 A1* | 4/2006 | Fritzler | G01T 1/1614 257/291 |
| 2007/0263764 A1 | 11/2007 | McCallum | |
| 2008/0156993 A1 | 7/2008 | Weinberg | |
| 2012/0265050 A1 | 10/2012 | Wang | |
| 2013/0237818 A1* | 9/2013 | Herrmann | A61B 6/032 600/436 |
| 2016/0194558 A1* | 7/2016 | Riddle | G01T 1/16 250/390.11 |

FOREIGN PATENT DOCUMENTS

| | | |
|---|---|---|
| WO | 2016/046216 | 3/2016 |
| WO | 2017025888 | 2/2017 |

\* cited by examiner

HYBRID PET / CT IMAGING DETECTOR

CROSS REFERENCE TO RELATED APPLICATIONS

This application is the U.S. National Phase application under 35 U.S.C. § 371 of International Application No. PCT/IB2016/054493, filed Jul. 28, 2016, published as WO 2017/025842 on Feb. 16, 2017, which claims the benefit of U.S. Provisional Patent Application No. 62/202,414 filed Aug. 7, 2015. These applications are hereby incorporated by reference herein.

FIELD OF THE INVENTION

The following generally relates to an imaging detector and more particularly to a hybrid positron emission (PET)/computed tomography (CT) imaging detector configured to detect both gamma rays and X-rays with a same detector.

BACKGROUND OF THE INVENTION

Positron emission tomography (PET) imaging is a functional imaging modality that generates and displays three-dimensional (3-D) tomographic images of distribution of radioactive isotopes injected into the body. While PET images provide quantitative representations of isotope distribution, they lack structural information about the anatomical structure of the surrounding tissues where the isotope is distributed. Computed tomography (CT) imaging generates 3-D tomographic images with structural information of anatomical tissue. PET and CT images have been combined (e.g., overlaid, fused, etc.) to provide functional information with an anatomical frame of reference.

PET and CT datasets can be acquired individually with a standalone PET gantry and a standalone CT gantry. PET and CT datasets can also be acquired with a single system that includes both a PET gantry portion and a CT gantry portion. With this configuration, the PET and CT gantry portions are physically spaced apart from each other along the scanning axis and have separate and distinct imaging planes. The PET and CT gantry portions are consecutively employed, moving the subject or object in between scans from one gantry portion to the other, and PET and CT datasets are acquired independently in that the PET dataset is not acquired with the CT gantry portion, and the CT dataset is not acquired with the PET gantry portion.

Unfortunately, with the above noted configurations, patient movement, voluntary and/or involuntary, between PET and CT scans may result in miss-registration of combined PET and CT images. Furthermore, the patient is moved from one gantry/gantry portion to the other gantry/gantry portion between PET and CT scans, which increases total scan time. Moreover, standalone and connected systems require two separate gantries/gantry portions and supporting hardware for each, each adding to manufacturing and/or service complexity and/or cost.

SUMMARY OF THE INVENTION

Aspects of the present application address the above-referenced matters and others.

According to one aspect, an imaging system includes a radiation sensitive detector array with at least one ring. The at least one ring includes a first layer configured to detect gamma radiation and X-ray radiation and generate signals indicative thereof and a second layer configured to detect only gamma radiation and generate a signal indicative thereof. The first and second layers are concentric closed rings of the at least one ring.

In another aspect, a method includes detecting gamma radiation with a first layer of a dual layer PET/CT detector in response to imaging in PET mode, detecting gamma radiation with a second layer of the dual layer PET/CT detector in response to imaging in PET mode, and generating PET image data with the gamma radiation detected with the first and second layers. The method further includes detecting X-ray radiation with the first layer of the dual layer PET/CT detector in response to imaging in CT mode and generating CT image data with the X-ray radiation detected with the first layer. The method further includes visually displaying the PET image data and the CT image data.

In another aspect, an imaging detector array includes at least one ring that includes a plurality of detector modules, each detector module including a plurality of detectors. Each detector includes a first layer having a plurality of first pixels configured to detect gamma radiation and X-ray radiation and generate signals indicative thereof, and a second layer having a plurality of second pixels configured to detect only gamma radiation and generate a signal indicative thereof. The first and second layers are vertically stacked one on top of the other in a direction of incident gamma radiation and X-ray radiation.

Still further aspects of the present invention will be appreciated to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
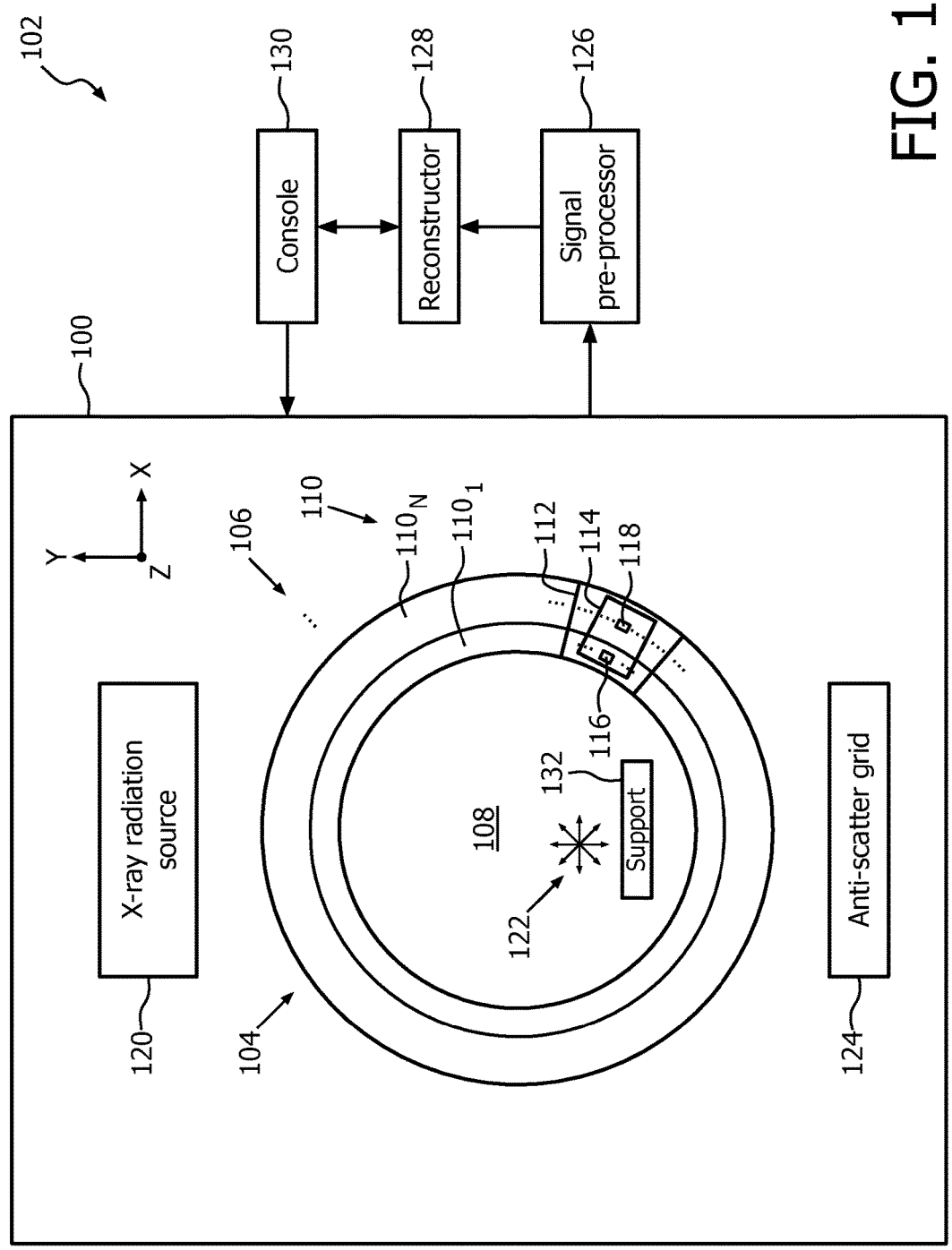
FIG. 1 schematically illustrates an example imaging system with a hybrid PET/CT imaging detector.

FIG. 1 schematically illustrates a hybrid PET/CT scanner 102.

A detector array 104 includes one or more detector rings 106 arranged with respect to each other along a z-axis. Each detector ring 106 includes an aperture, which surrounds an examination region 108. The illustrated detector ring 106 includes at least two layers 110, including an inner layer $110_1, \ldots,$ and an outer layer $110_N$, where N is a positive integer. The inner and outer layers $110_1$ and $110_N$ respectively are closed rings, concentrically arranged with respect to each other in an x-y plane. In the illustrated embodiment, the detector array 104 and hence the layers $110_1$ and $110_N$ are disposed in a single PET/CT gantry 100.

In one instance, the layers 110 include a plurality of modules 112, each module 112 including a plurality of detectors 114, and each detector 114 including a sub-portion of the inner and outer layers $110_1$ and $110_N$. In this instance, the individual modules 112 are attached to the hybrid PET/CT scanner 102 to construct the detector ring 106. A detector 114 includes first and second layer $110_1$ and $110_N$ pixels 116 and 118 configured to detect radiation in a predetermined energy band(s) and generate and output signals indicative thereof. As described in greater detail below, the inner layer $110_1$ is configured as a single layer that detects both gamma rays and X-rays with the same pixels 116, and the outer layer $110_N$ is configured to detect only gamma rays with the pixels 118.

For CT imaging, only the inner layer $110_1$ is activated to detect X-ray radiation. For PET imaging, both the inner and the outer layers $110_1$ and $110_N$ are activated to detect gamma radiation. As such, 511 keV photons photo-electrically attenuated by the inner layer $110_1$ and/or energy from Compton scattered gamma rays deposited in the inner layer $110_1$ are detected and can be combined with the output from the outer layer $110_N$. This may mitigate data loss due to gamma ray absorption in the inner layer $110_1$. Furthermore, since the inner layer $110_1$ contributes to the overall gamma attenuation, the outer layer $110_N$ width can be decreased. Thus, cost can be reduced without loss of PET information.

The detector array 104 described herein may also reduce manufacturing and/or service complexity and cost relative to a system with separate and independent PET and CT detector modules. For example, the detector 114 can be built, assembled into the modules 112, and the whole scanner 102 can be assembled in one facility on one assembly line, which simplifies construction and assembly, providing a logistical advantage. Moreover, the alignment of PET and CT images during registration can be improved as patient movement between PET and CT scans is mitigated, which may also reduce overall scan time.

An X-ray radiation source 120 is configured to generate and transmit X-ray radiation that traverses the examination region 108. X-rays include radiation having an energy in the band from 20 keV to 120 keV. As described in greater detail below, the X-ray radiation source 112 can be fixedly or moveably (rotationally and/or translationally) coupled to the scanner 102. Gamma radiation is emitted via positron annihilation events during radioactive decay 122 of a radioactive isotope of an agent inside the examination region 108 and traverses the examination region 108. Gamma rays include radiation having an energy in the energy band from 120 keV to 520 keV.

In the illustrated embodiment, an anti-scatter grid 124 is employed. The anti-scatter grid (ASG) 124 is disposed adjacent to a radiation receiving face of the inner layer $110_1$. In one instance, the anti-scatter grid 124 includes septa with X-ray absorbing material (e.g., lead, tungsten, etc.) that attenuate scatter X-ray radiation. As described in greater detail below, the anti-scatter grid 124 is configured as an arc or a closed ring and is moveable (rotationally and/or translationally) or fixed with respect to the examination region 108. In another embodiment, the anti-scatter grid 124 is omitted.

Signal pre-processing circuitry 126 processes the signal from the detector array 104. For the inner layer $110_1$, this includes energy discriminating and binning the detected gamma and/or X-ray radiation based on a set of predetermined energy thresholds of interest. For example, detected gamma rays can be binned into energy bins such as 120-480 keV and 480-520 keV during PET imaging, and detected X-rays can be binned into energy bins such as 0-40 keV, 40-80 keV and 80-120 keV CT during imaging. Other numbers of bins and/or bin widths are contemplated herein.

For PET mode, the pre-processing circuitry 126 identifies coincident gamma pairs detected in the outer layer $110_N$ by identifying photons detected in temporal coincidence (or near simultaneously) along a line of response (LOR) and generates event by event or list mode data indicative thereof. The data may also include time-of-flight (TOF) information, which allows the pre-processing circuitry 126 to estimate the location of an event along a LOR.

For PET mode, the pre-processing circuitry 126 extrapolates the position of 511 keV photons detected by the inner layer $110_1$ (e.g., from the above example energy bin 480-520 keV) to the corresponding PET pixels in the second layer $110_N$. Furthermore, the pre-processing circuitry 126, for Compton scattered gamma rays, utilizes the energy information from, e.g., the above example energy bin 120-480 keV, and the corresponding timing to sum Compton split photons back into their original 511 keV energy level. These events are then assigned to the corresponding PET pixels in the second layer $110_N$.

A reconstructor 128 is configured to reconstruct PET and CT volumetric image data and/or images from the detector 104 output. For PET, this includes reconstructing the data the outer layer $110_N$ along with the PET data from the inner layer $110_1$ that was mapped to the outer layer $110_N$. For CT, this includes reconstructing data selectively from one or more particular energy bins for spectral (energy dependent) imaging and/or combining the data from all of the CT bins and reconstructing conventional CT image data over the CT energy spectrum. The reconstructor 128 can be a single reconstructor or include a PET reconstructor and a CT reconstructor.

A computer is configured as an operator console 130 and includes a human readable output device such as a monitor or display and an input device such as a keyboard and mouse. Software resident on the operator console 130 allows the operator to interact with the hybrid PET/CT scanner 102, e.g., via a graphical user interface (GUI) or otherwise. This interaction may include selecting an imaging mode (e.g., PET mode and/or CT mode), initiating scanning, etc. A subject support 132 supports a subject or an object in the examination region 108.

Figure 2:
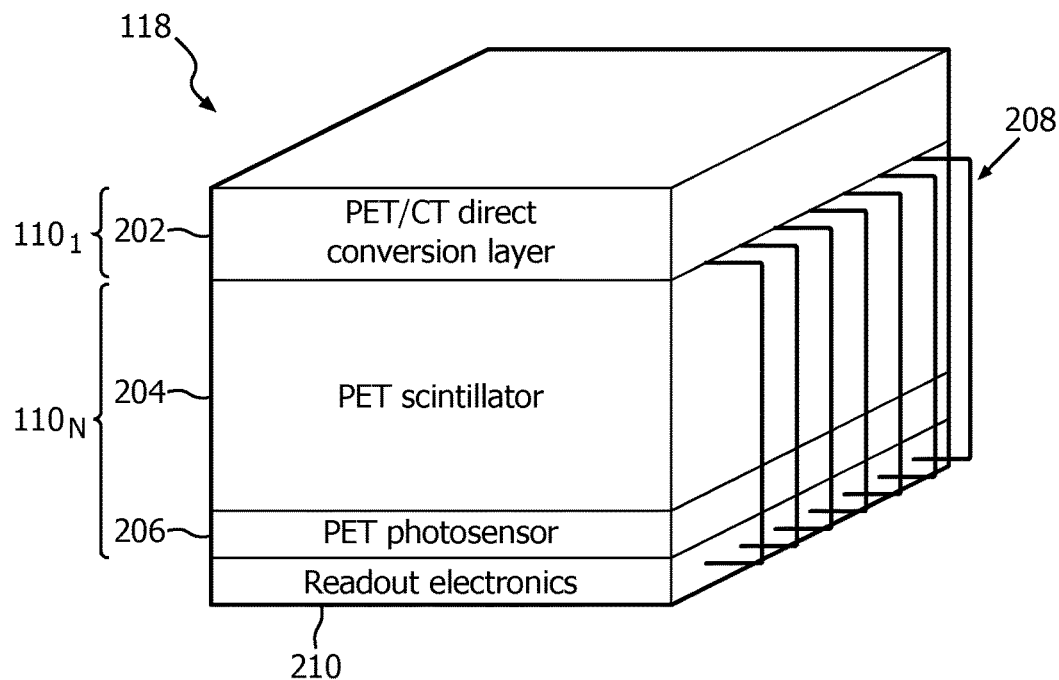
FIG. 2 schematically illustrates an example of a direct conversion based hybrid PET/CT imaging detector.

FIG. 2 schematically illustrates an example of a module 118 for a two-layer (N=2) ring 106.

The inner layer $110_1$ includes a PET/CT direct conversion material 202, which directly converts absorbed incident gamma and/or X-ray radiation to electrical signals (e.g., voltage or electrical current pulses) having a peak height indicative of the energy of the absorbed incident gamma and/or X-ray radiation. Examples of a suitable direct conversion material include Cadmium Zinc Telluride (CZT), silicon strips, and/or other materials. The attenuation in the PET/CT direct conversion material 202 is quantifiable and set by a thickness of the direct conversion material.

The outer layer $110_2$ includes a PET scintillator 204 optically coupled to a PET photosensor 206. Examples of suitable scintillation materials for the PET scintillator 204 include lutetium-yttrium oxyorthosilicate (LYSO), Bismuth germanium oxide (BGO), and/or other scintillation material that absorbs 511 keV gamma rays. The photosensor 206 is tuned to sense light emitted by the PET scintillator 204 and generates an electrical signal indicative thereof.

In one instance, the inner and outer layers $110_1$ and $110_2$ are fixedly coupled together. In another instance, the inner and outer layers $110_1$ and $110_2$ are removeably coupled together. With this instance, the individual layers 110 can be separated and independently serviced, which may reduce cost since an entire detector need not be replaced. In the illustrated embodiment, the direct conversion material 202 is coupled to a radiation receiving face of the PET scintillator 204.

A circuit 208 is electrically coupled to the direct conversion material 202 and the readout electronics 210. The circuit 208 routes signals from the direct conversion material 202 to readout electronics 210, which route signals from the inner and outer layers 110 to the signal pre-processing circuitry 116 (FIG. 1). In this example, the circuit 208 is disposed along a side of the module 118 that is perpendicular to the gamma ray and X-ray receiving sides of the PET/CT direct conversion material 202 and the PET scintillator 204.

With this configuration, the signal pre-processor 116 (FIG. 1) includes an energy-discriminator for the output of the inner layer $110_1$ that discriminates the electrical signals from the direct conversion material 202, e.g., with one or more comparators, each having a different predetermined energy threshold value, which corresponds to an energy of interest. A counter increments a count value for each threshold in response to the output of the corresponding comparator satisfying the threshold. A binner energy-bins the signals and, hence, the detected gamma rays or X-rays multiple energy bins based on the counts.

In a variation, the direct conversion material 202 includes an encapsulate material with particles supporting quantum dots of scintillation material embedded therein. In one instance, the direct conversion material 202 is a single layer with different groups of quantum dots for different energy ranges homogeneously distributed in the encapsulate material. In another instance, the direct conversion material 202 includes multiple layers, each layer including a single group of the quantum dots for a single energy range of the different energy ranges.

An example of a quantum dot direct conversion detector is described in application Ser. No. 62/202,397, filed Aug. 7, 2015, and entitled "QUANTUM DOT BASED IMAGING DETECTOR," the entirety of which is incorporated herein by reference. An example of an encapsulate material with quantum dots of scintillation material embedded therein is described in EP 14186022.1, filed Sep. 23, 2014, and entitled "Encapsulated materials in porous particles," the entirety of which is incorporated herein by reference.

Figure 3:
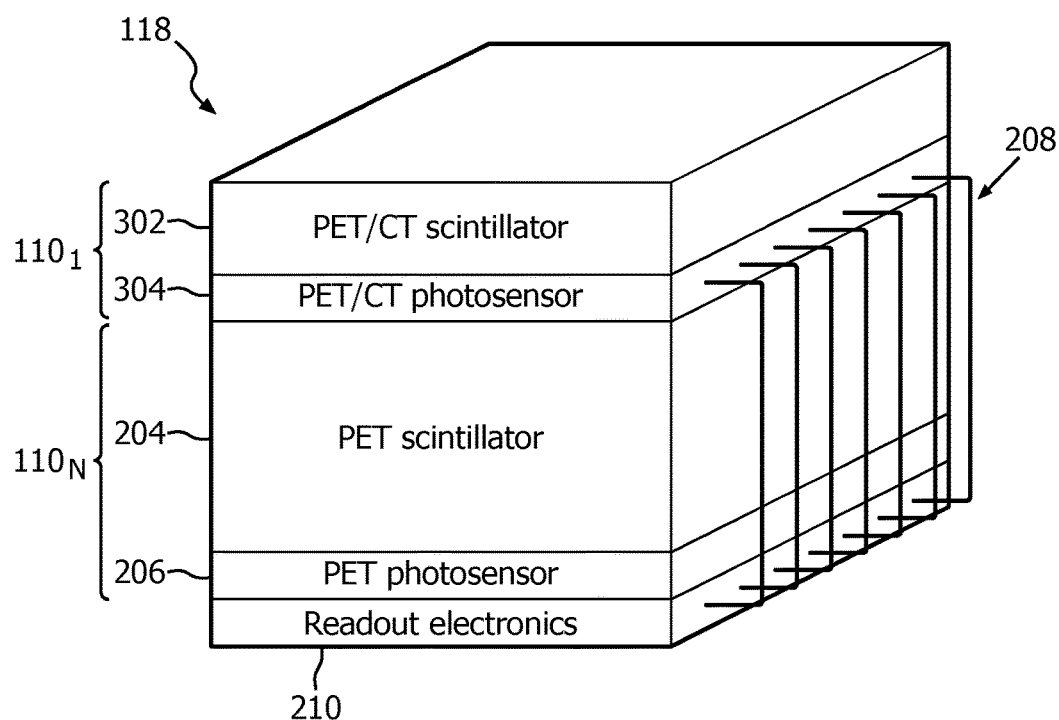
FIG. 3 schematically illustrates an example of a scintillator/photosensor based hybrid PET/CT imaging detector.

FIG. 3 schematically illustrates another example of a module 118 for a two-layer (N=2) ring 106. In this embodiment, the outer layer $110_2$ and the readout electronics 210 are the same as described in connection with FIG. 2.

In this example, the inner layer $110_1$ includes an indirect conversion structure, which includes a scintillation material 302 optically coupled to a photosensor 304. In general, gamma or X-rays absorbed by the scintillation material 302 are converted to light photons, which are sensed by the photosensor 304, which generates an electrical signal indicative thereof.

An example of a suitable scintillation material 302 is gadolinium oxysulfide (GOS). Another example is LYSO, an encapsulate material with particles supporting quantum dots of scintillation material embedded therein such as that described in application Ser. No. 62/202,397, filed Aug. 7, 2015, and entitled "QUANTUM DOT BASED IMAGING DETECTOR".

Where the photosensor 304 is coupled to a flip chip, signals are routed from the photosensor 304 through the flip chip to the circuit 208 as described herein and/or otherwise to the readout electronics 210. Likewise, the circuit 208 is disposed along a side of the module 118 as described herein, but other configurations are contemplated herein. Likewise, the inner and outer layers $110_1$ and $110_2$ are fixedly or removeably coupled together.

With this configuration, the signal pre-processor 116 (FIG. 1) includes a pulse shaper that processes the signal (which can first be amplified) from the PET/CT photosensor 304 and generates a pulse (e.g., voltage, current, etc.) indicative of the energy of the detected radiation.

Figure 4:
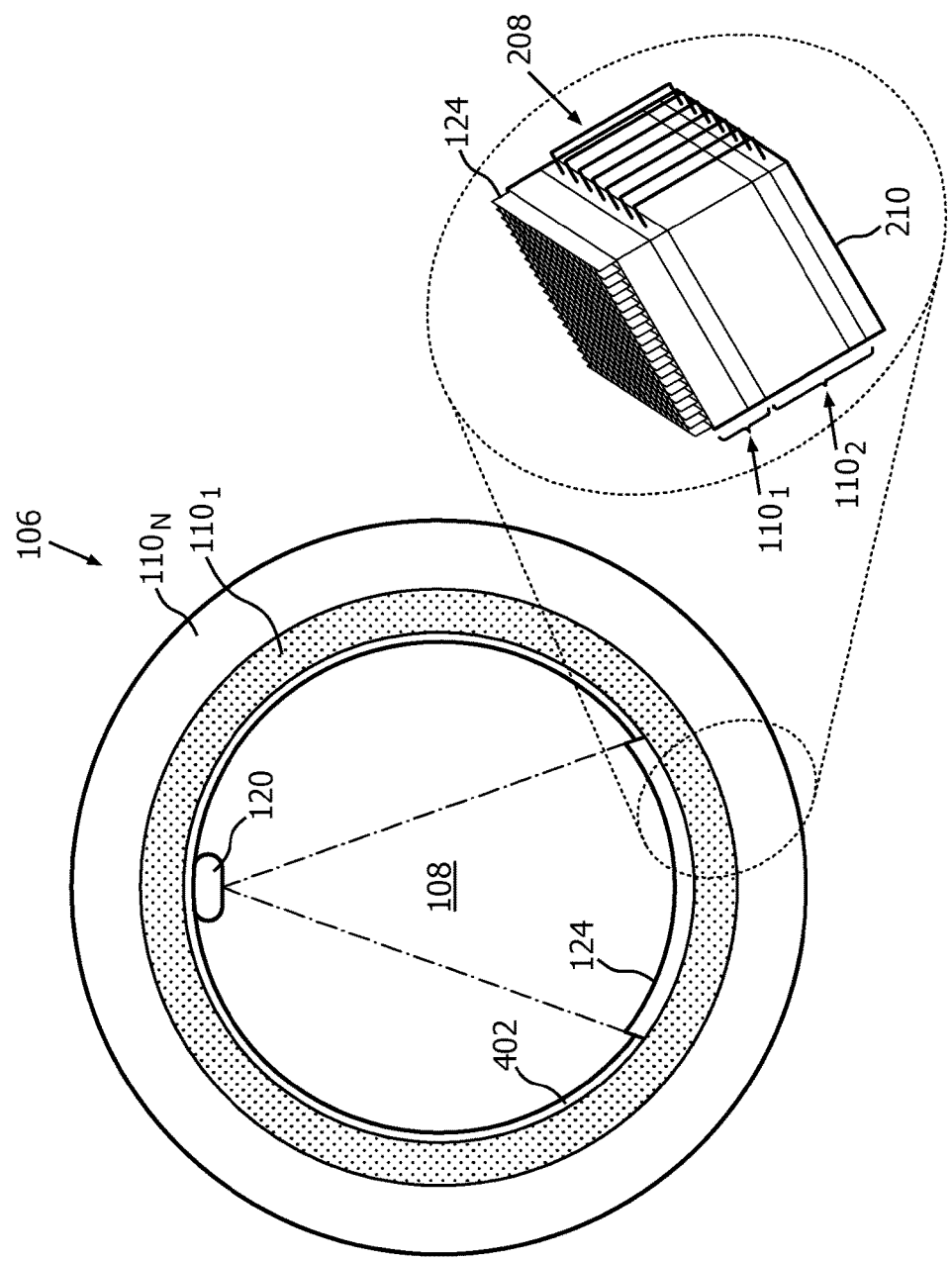
FIG. 4 schematically illustrates a front view showing a moveable support supporting an X-ray radiation source and anti-scatter grid.
Figure 5:
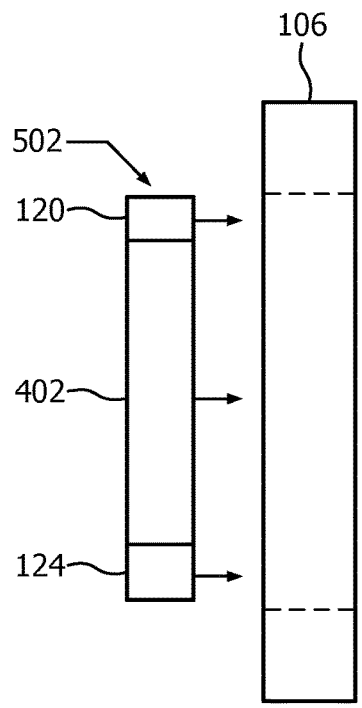
FIG. 5 schematically illustrates a side view of the configuration of FIG. 4 with the X-ray radiation source and the anti-scatter grid outside of the examination region.
Figure 6:
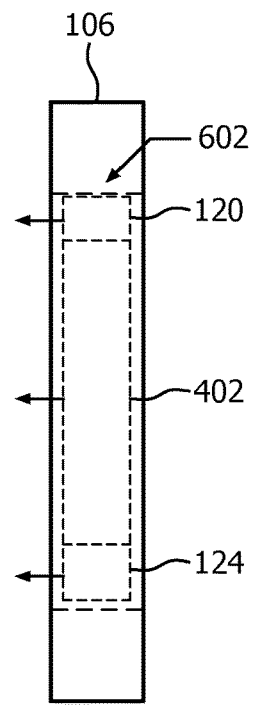
FIG. 6 schematically illustrates a side view of the configuration of FIG. 4 with the X-ray radiation source and the anti-scatter grid inside of the examination region.

FIGS. 4, 5 and 6 schematically illustrate a detector ring 106 in connection with an example X-ray radiation source 120 and the anti-scatter grid 124. FIG. 4 shows a view looking into the aperture of the ring 106 into the examination region 108. FIGS. 5 and 6 show side views of the detector ring 106 respectively with the X-ray radiation source 120 and the anti-scatter grid 124 outside of (FIG. 5) and inside of (FIG. 6) the examination region 108.

In this example, a carriage or support 402 supports both an X-ray tube 120 and the anti-scatter grid 124. The support 402 and hence the X-ray tube 120 and the anti-scatter grid 124 are moveably mounted to the scanner 102 to translate at least between a position 502 (FIG. 5) outside of the examination region 108 and a position 602 (FIG. 6) inside of the examination region 108. The support 402 and hence the X-ray tube 120 and the anti-scatter grid 124 are also configured to rotate around the examination region 108.

The support 402 can be coupled in the PET/CT scanner 102 via slide, ball, etc. bearings, and moved between the positions 502 and 602 via a motor and a belt, chain, lead screw, gears, etc. A controller would drive the motor based on whether scanner 102 is in PET mode or CT mode. In PET mode, the support 402 is placed at position 502 for PET imaging, and in CT mode, the support 402 is placed at position 602 for CT imaging.

It is to be appreciated that FIGS. 4-6 are provided to show the X-ray tube 120 and the anti-scatter grid 124 attached to a same support (the same support 402) configured to move out of and into the examination region 108 respectively for PET and CT imaging. It is to be understood the relative size and/or position of the layers 106, the support 402, the X-ray tube 120, and the anti-scatter grid 124 are not limiting.

Figure 7:
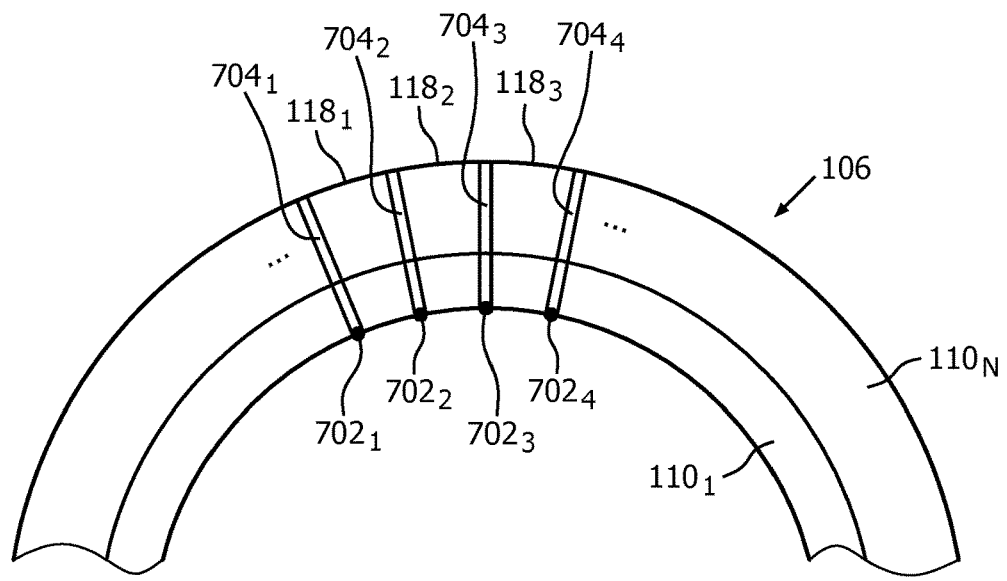
FIG. 7 schematically illustrates an example of another configuration of the X-ray source.

FIG. 7 schematically illustrate a variation where the X-ray radiation source 120 includes solid state x-ray generators $702_1$, $702_2$, $702_3$, $702_4$, ... located in gaps $704_1$, $704_2$, $704_3$, $704_4$, ... between module $118_1$, $118_2$, $118_3$, $118_4$, ... throughout the ring 106. The x-ray generators $702_1$, $702_2$, $702_3$, $702_4$, ... are pulsed in sequence to obtain CT data for the full circumference of the ring.

In one instance, the anti-scatter grid 124 can be attached to and moved by the support 402 as discussed in connection with FIGS. 4, 5 and 6 in coordination with activation of the generators $702_1$, $702_2$, $702_3$, $702_4$, .... In a variation, the anti-scatter grid 124 is a full circle and translates between 505 and 602, but does not rotate around the examination region like in FIGS. 4-6.

Figure 8:
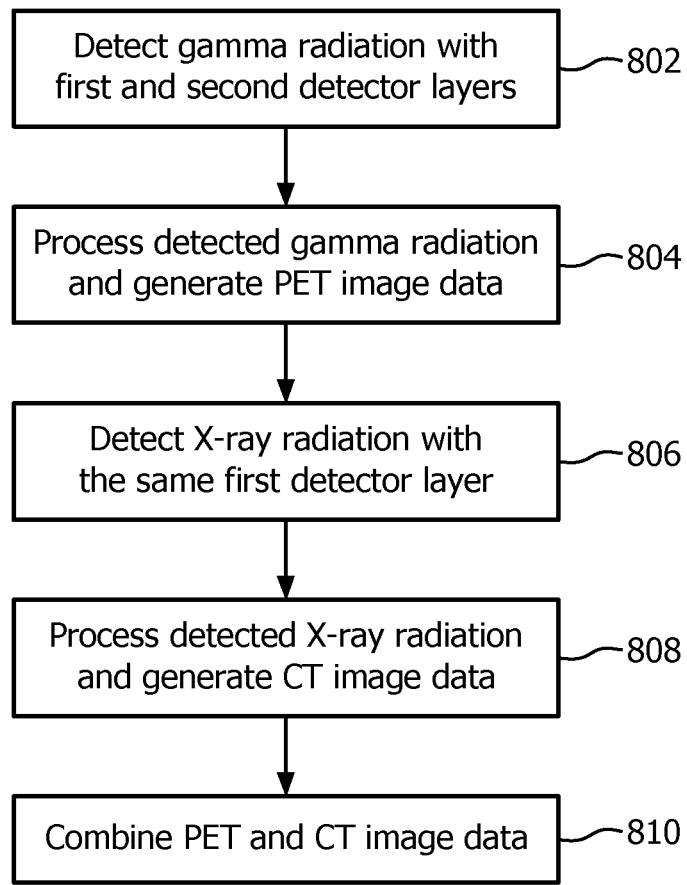
FIG. 8 illustrates an example method in accordance with an embodiment herein.

FIG. 8 illustrates an example method in accordance with an embodiment herein.

It is to be appreciated that the ordering of the below acts is for explanatory purposes and not limiting. As such, other orderings are also contemplated herein. In addition, one or more of the acts may be omitted and/or one or more other acts may be included.

At 802, gamma radiation is detected by a first layer and a second layer of a dual layer imaging detector of an imaging system and the first and second layers generate first and second signals indicative thereof.

At 804, the first and second signals are processed, which generates PET image data.

At 806, X-ray radiation is detected by the same first layer of the dual layer imaging detector of the imaging system and the first layer generates third signal indicative thereof.

At 808, the third signals are processed, which generates CT image data.

At 810, the PET and CT image data are combined and displayed.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
   a radiation sensitive detector array with at least one detector ring including:
     a first layer configured to detect gamma radiation and X-ray radiation and generate signals indicative thereof;
     a second layer configured to detect only gamma radiation and generate a signal indicative thereof,
     wherein the first and second layers are concentric rings of the at least one detector ring; and
     a signal pre-processor configured to process the signals indicative of the gamma radiation detected by the first layer, the X-ray radiation detected by the first layer, and the gamma radiation detected by the second layer,
     wherein the signal pre-processor is configured to bin the gamma radiation detected by the first layer into a predetermined set of PET energy bins based on predetermined set of PET energy thresholds, and bin the X-ray radiation detected by the first layer into a predetermined set of CT energy bins based on predetermined set of CT energy thresholds.

2. The imaging system of claim 1, further comprising:
   a single gantry, wherein the at least one detector ring with the concentric first and second layers is disposed in the single gantry.

3. The imaging system of claim 1, further comprising:
   a reconstructor configured to reconstruct the processed signals indicative of the gamma radiation detected by the first layer, the X-ray radiation detected by the first layer, and the gamma radiation detected by the second layer and generate positron emission tomography (PET) and computed tomography (CT) image data.

4. The imaging system of claim 3, wherein the reconstructor configured to reconstruct the X-ray radiation detected by the first layer from a predetermined one of the set of CT energy bins.

5. The imaging system of claim 1, wherein the signal pre-processor is configured to extrapolate a position of 511 keV photon in the set of PET energy bins to a corresponding pixel location of the second layer.

6. The imaging system of claim 1, wherein the signal pre-processor is configured to utilize energy information from the set of PET energy bins and PET and CT timing information to sum Compton photons absorbed in part in the first layer and in part in the second layer into a 511 keV photon for a corresponding pixel location of the second layer.

7. The imaging system of claim 1, wherein the signal pre-processor configured to identify a coincident gamma pair along a line of response based on the gamma radiation detected by the second layer.

8. The imaging system of claim 7, wherein the signal pre-processor is configured to estimate a location of the coincident gamma pair along the line of response.

9. The imaging system of claim 1, wherein the first layer includes a direct conversion material, wherein the direct conversion material includes Cadmium Zinc Telluride, a plurality of silicon strips, or a solid state garnet.

10. The imaging system of claim 1, wherein the first layer includes a direct conversion material, wherein the direct conversion material includes an encapsulate material with quantum dots of scintillation material embedded therein.

11. The imaging system of claim 1, wherein the first layer includes a scintillator optically coupled to a photosensor.

12. The imaging system of claim 1, further comprising:
    an X-ray radiation source configured to move out of an examination region to acquire PET data and into the examination region to acquire CT data.

13. The imaging system of claim 1, further comprising:
    anti-scatter grid configured to move out of an examination region for a PET scan and into the examination region for a CT scan.

14. A method, comprising:
    detecting gamma radiation with a first layer of a dual layer PET/CT detector in response to imaging in PET mode;
    detecting gamma radiation with a second layer of the dual layer PET/CT detector in response to imaging in PET mode;
    generating PET image data with the gamma radiation detected with the first and second layers;
    detecting X-ray radiation with the first layer of the dual layer PET/CT detector in response to imaging in CT mode;
    energy-binning the gamma radiation detected with the first layer in an energy bin including 511 keV;
    energy-binning the X-ray radiation detected with the first layer in a predetermined set of energy bins over an energy range from 10 keV to 120 keV; and
    generating CT image data with the X-ray radiation detected with the first layer; and
    visually displaying the PET image data and the CT image data.

15. The method of claim 14, further comprising:
    extrapolating a position of 511 keV photon from the energy-binned the gamma radiation to a pixel location of the second layer.

16. The method of claim 14, further comprising:
    energy-binning the gamma radiation detected with the first layer in an energy bin with a window from 120 keV to 480 keV;
    identifying split Compton photons absorbed in the first layer based on the energy-binned gamma radiation; and
    summing the identified split Compton photon absorbed in the first layer with a remaining portion of the split Compton photon absorbed in the second layer based on timing information for the first and second layers into a 511 keV photon for a pixel in the second layer.

17. The method of claim 14, further comprising:
selectively reconstructing the energy binned X-ray radiation for at least one of the bins of the set of energy bins.

18. The method of claim 14, further comprising:
superimposing the CT image data over the PET image data.

19. An imaging detector array, comprising:
at least one ring that includes a plurality of detector modules, each detector module including a plurality of detectors, each detector including:
- a first layer having a plurality of first pixels configured to detect gamma radiation and X-ray radiation and generate signals indicative thereof;
- a second layer having a plurality of second pixels configured to detect only gamma radiation and generate a signal indicative thereof,
- wherein the first and second layers are vertically stacked one on top of the other in a direction of incident gamma radiation and X-ray radiation; and
- a signal pre-processor configured to process the signals indicative of the gamma radiation detected by the first layer, the X-ray radiation detected by the first layer, and the gamma radiation detected by the second layer,
- wherein the signal pre-processor is configured to bin the gamma radiation detected by the first layer into a predetermined set of PET energy bins based on predetermined set of PET energy thresholds, and bin the X-ray radiation detected by the first layer into a predetermined set of CT energy bins based on predetermined set of CT energy thresholds.

* * * * *